(12) United States Patent
Jussel et al.

(10) Patent No.: US 8,465,681 B2
(45) Date of Patent: Jun. 18, 2013

(54) METHOD FOR OPERATING A PRESS FURNACE, AND PRESS FURNACE

(75) Inventors: Rudolf Jussel, Feldkirch-Tosters (AT); Harald Bürke, Frastanz (AT)

(73) Assignee: Ivoclar Vivadent AG, Schaan (LI)

( * ) Notice: Subject to any disclaimer, the term of this patent is extended or adjusted under 35 U.S.C. 154(b) by 236 days.

(21) Appl. No.: 11/975,480

(22) Filed: Oct. 20, 2007

(65) Prior Publication Data
US 2008/0099939 A1    May 1, 2008

(30) Foreign Application Priority Data
Oct. 27, 2006 (DE) .......................... 10 2006 050 830

(51) Int. Cl.
*A61C 13/00* (2006.01)

(52) U.S. Cl.
USPC ................ 264/16; 264/40.1; 264/17; 264/18; 264/19; 425/135; 425/145; 425/149; 425/162; 425/167; 425/169; 425/136

(58) Field of Classification Search
USPC ................. 264/40.1, 16, 17, 18, 19; 425/169, 425/136, 135, 145, 149, 162, 167, 178; 432/32, 432/205, 51; 219/390; 72/342.8, 20.1
See application file for complete search history.

(56) References Cited

U.S. PATENT DOCUMENTS

| 5,395,565 A   | * | 3/1995  | Nagaoka et al. | ............. 264/40.5 |
| 6,180,922 B1  | * | 1/2001  | Rohner et al.  | ................ 219/390 |
| 6,303,059 B1  |   | 10/2001 | Foser          |                      |

FOREIGN PATENT DOCUMENTS

| AU | 617064  | B2 | 8/1991 |
| CA | 2282901 | A1 | 3/2000 |
| CA | 2299009 | A1 | 9/2000 |

\* cited by examiner

*Primary Examiner* — Yogendra Gupta
*Assistant Examiner* — Ninh Le
(74) *Attorney, Agent, or Firm* — Hodgson Russ LLP

(57) ABSTRACT

The invention relates to a method for operating a press furnace, in particular for dental materials, with an embedding compound into which the preferably ceramic dental material can be introduced via a press ram (26), the speed of penetration of the press ram (26) being detected, wherein, during the pressing operation, an increase in the speed of penetration and/or a decrease is detected, and, based on this, a signal is output.

5 Claims, 2 Drawing Sheets

METHOD FOR OPERATING A PRESS FURNACE, AND PRESS FURNACE

CROSS-REFERENCE TO RELATED APPLICATIONS

This application claims foreign priority benefits under 35 U.S.C. §119(a)-(d) from German patent application ser. no. 10 2006 050 830.0 filed Oct. 27, 2006.

TECHNICAL FIELD

The present invention relates to a method for operating a press furnace with an embedding compound into which the preferably ceramic dental material can be introduced via a press ram, and to a press furnace suitable for use with the foregoing method.

BACKGROUND OF THE INVENTION

A press furnace of this kind is known from, for example, U.S. Pat. No. 6,303,059. This press furnace is distinguished by a special control method in which a pressing force is detected and the decrease in the speed of penetration into an embedding compound is used as a switch-off signal for the pressing operation.

In the case of a press furnace operating free of faults, this makes it possible to ensure an optimized filling of the hollow cavities and to a certain extent also a secondary compaction of the introduced ceramic dental restoration material. To achieve this, a predetermined switch-off threshold, for example 0.3 mm per 3 minutes, is established, and, if the speed of penetration falls below this value, the press plunger is switched off. To avoid bursting of the embedding compound muffle, the pressing force should lie below a certain value which is at a safety interval from the maximum possible pressing force.

It is true that this method for controlling the speed of penetration is effective per se and has proven itself in practice. However, it would be desirable to further reduce the cycle time for the pressing, without entailing the risk of a poorer restoration result. In this connection, it is particularly important to ensure a sufficient repressing time, since the strength of the dental restoration is mainly defined in this way.

Various measures have been disclosed for optimizing the time at which the furnace is switched off. For example, AU 617064B2 discloses the detection of a pressure increase at a predetermined speed of advance of the press ram. In this solution, however, the plunger speed additionally has to be detected, and, as is known, every additional sensor which is provided, and whose output signal is used for control purposes, detracts from the reliability of the control.

Moreover, it has already been proposed to configure the embedding compound in such a way that it is slightly more elastic and thus less inclined to formation of cracks. This is indeed possible in principle by corresponding provision of a mixture suitable for this purpose. However, a disadvantage is that the hollow spaces that are intended for the formation of the dental restorations are then slightly less accurate in terms of their shape, with the result that the dental restoration parts then often have to be worked in order to remove material, which in turn lengthens the production process.

By contrast, the object of the invention is to make available a method for operating a press furnace and a press furnace, which method and press furnace permit the use of embedding compounds that are especially accurate in terms of their shape, without the pressing force having to be reduced for safety reasons, or without increased risk of bursting of the embedding composition muffle.

OBJECTS AND SUMMARY OF THE INVENTION

The operating method according to the invention for a press furnace permits a comparatively rapid cycle time with a fairly high pressing force. The deviation of the speed of penetration from a predetermined profile is detected according to the invention, it being understood that different muffles in principle have different speed of penetration profiles. In dental restoration parts, however, press channels are always provided which are adjoined by hollow cavities intended for the formation of the dental restoration parts. When the ceramic compound penetrates into the press channels, the speed of penetration typically drops, since the friction there is quite high and increases the longer the effective friction surface between the ceramic dental material and the channel wall. As soon as the leading edge of the embedding compound has reached the hollow cavity, however, the friction does not continue to increase or does so only minimally; this accordingly corresponds to the speed of penetration remaining constant until the hollow cavity is filled.

Even though the length of the press channels and the size of the hollow cavities differ from muffle to muffle, this basic speed of penetration profile always exists in principle, followed, in a third pressing time phase, by a further decrease in the speed of penetration, during which time phase a compaction of the dental material takes place.

According to the invention, it has now been found that the speed of penetration deviates from this basic profile, namely either increases or decreases less than corresponds to the speed of penetration profile. This means in fact that, at this point in time, a further hollow cavity opens up, typically when the muffle bursts. According to the invention, however, the dental restoration part can surprisingly be used, at least if the pressing operation is relatively far advanced.

In any event, the signal according to the invention permits the reactions suitable for this purpose, for example a discontinuation of the pressing operation.

The monitoring of the speed of penetration profile is also advantageous if objects are positioned unfavorably in the embedding compound, for example by the dental technician, and if this leads, for example, to a weakening of the embedding compound or to an increased tendency to cracking.

It will be appreciated that it is particularly expedient if the error discontinuation criterion according to the invention is linked to a standard discontinuation criterion which, as has already been made known, detects when the speed of penetration drops below a predetermined threshold value. According to the invention, it is particularly expedient if the actual value of the speed of penetration is continuously monitored, for example with a scanning rate of 0.1 to 10 seconds, preferably with a scanning rate of approximately 1 second.

The applied pressing force can also be used as an additional discontinuation criterion. In this connection, it is possible to exploit the fact that the spindle drive of the press ram typically has a maximum speed of advance and, if the dental material or the bursting muffle offers no resistance or too little resistance, the pressing force drops, and the press ram moves downward with a maximum speed of advance.

In an advantageous embodiment with a spindle drive for the press ram, the speed of advance can also be measured in revolutions per minute.

According to the invention, however, it is also particularly preferable that the press drive can be immediately stopped if a muffle bursts. This also very reliably avoids the muffles coming apart, so that it is possible to very reliably avoid damage to the firing space or the heating element or thermocouple.

According to the invention, tilting of the muffle parts and, consequently, damage to the thermocouple and its protective tube should, if possible, be completely avoided.

In another advantageous embodiment, provision is made that, during the pressing operation, an increase in the speed of penetration and/or a decrease in the injection force is detected, and, based on this, a signal is output.

In another advantageous embodiment, the signal is output when the increase in the speed of penetration and/or the decrease in the injection force occurs over a predetermined time period, which time period is in particular adjustable.

In another advantageous embodiment, the path of the press ram and/or the time and/or the force with which the press ram covers a defined path is measured, in particular continuously, or recurrently at regular time intervals, and, based on this, the speed of penetration and/or its changes are detected.

In another advantageous embodiment, the signal is a discontinuation signal via which the movement of the press ram is interrupted.

In another advantageous embodiment, the press ram is acted upon with a predetermined force, in particular a constant force, and the movement of the press ram is monitored starting from a start signal of a pressing cycle.

In another advantageous embodiment, the increase in the speed of penetration and/or the decrease in the injection force is used as an alternative discontinuation criterion for the pressing cycle, and the pressing cycle is ended.

In another advantageous embodiment, there is provision for the speed of penetration to be substantially constant near 0 toward the end of the pressing cycle and in particular during the secondary pressing time, and, if the speed of penetration deviates from constancy, that is to say upon renewed increase of the speed of penetration, an error signal is output.

In another advantageous embodiment, the pressing force, after reaching the nominal pressing force, in particular during the pressing cycle, is maintained substantially constant, and wherein the pressing force is switched off after a predetermined repressing time with a constant low speed of penetration, which can also be zero.

In another advantageous embodiment, as an alternative, a sudden decrease in the injection force, due to too short a readjustment time for the speed of penetration, can likewise be used for discontinuation of the pressing operation.

In another advantageous embodiment, an increase in the speed of penetration or a decrease in the injection force triggers a signal, which in particular indicates an error.

In another advantageous embodiment, a substantially constant pressing force acts on the press ram and the speed of penetration of the press ram into the embedding compound and/or the injection force can be detected continuously, and an increase in the speed of penetration and/or the decrease in the injection force outputs an error signal.

In another advantageous embodiment, the press furnace has a control unit that detects and stores the speed of penetration of the press ram and/or the injection force and compares it to a predetermined profile of the speed of penetration and of the injection force.

In another advantageous embodiment, the press ram is part of a force-generating device or interacts with such a device.

In another advantageous embodiment, the speed of penetration of the press ram and/or the injection force is detected via the force-generating device.

In another advantageous embodiment, the speed of penetration drops during a first pressing time phase and remains substantially constant during a second pressing time phase, and a deviation from at least one predetermined speed of penetration outputs a signal.

In another advantageous embodiment, the speed of penetration during a third pressing time phase drops and, in the event of a deviation from a predetermined speed of penetration profile, an error signal is output.

BRIEF DESCRIPTION OF THE FIGURES

Further advantages, details and features will become clear from the following description of an illustrative embodiment with reference to the drawing, in which.

DETAILED DESCRIPTION

Figure 1:
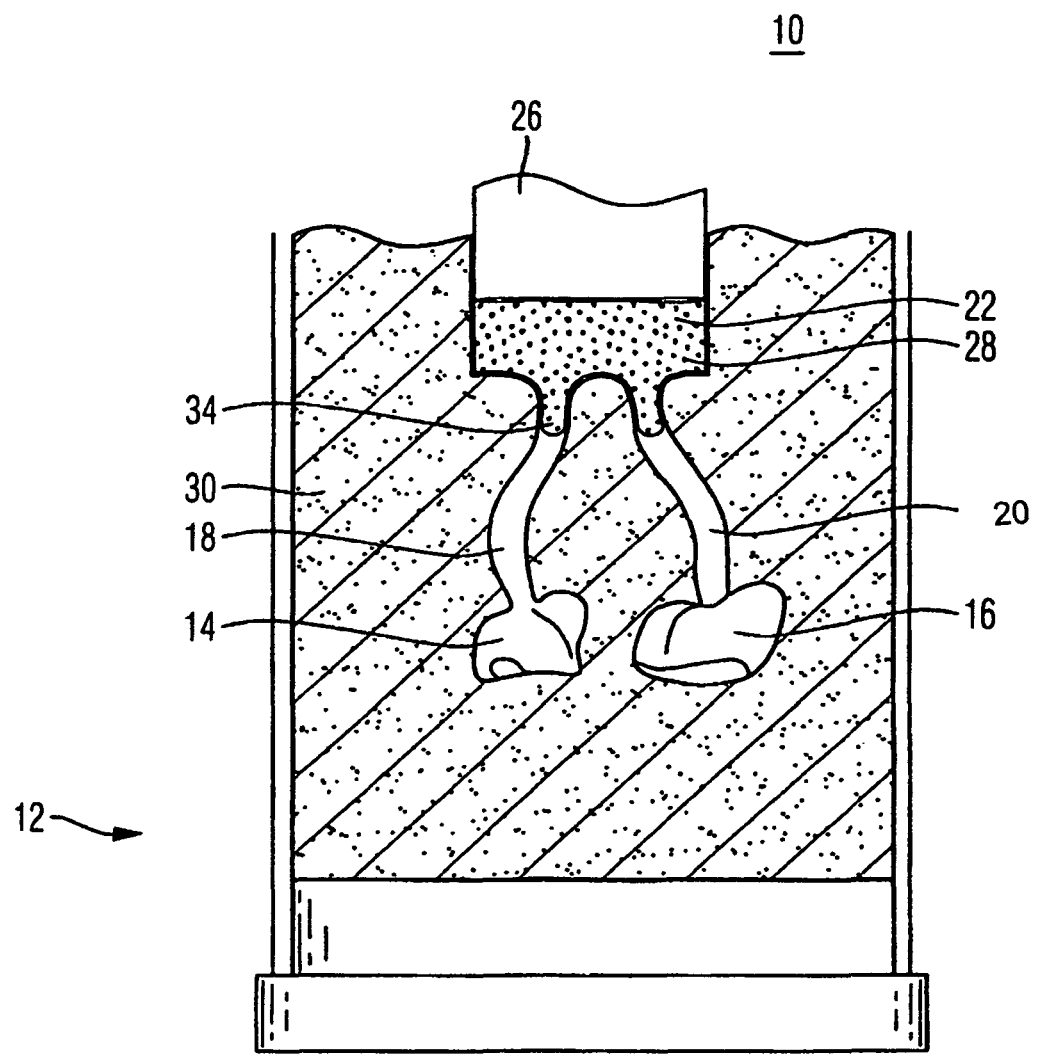
FIG. 1 shows a partial cross section through a press furnace according to the invention, depicting the muffle in a cutaway mold.

The press furnace 10 shown partially in FIG. 1 is intended for the placement of a muffle 12 into a firing cavity.

The muffle 12 is set in the firing cavity in a manner known per se. It has hollow cavities 14 and 16 that are intended as casting molds for the formation of dental restoration parts. The hollow cavities 16 and 14 are connected via press channels 18 and 20 to a preliminary press area 22 which is of substantially cylindrical design. A press ram 26 is mounted so as to slide in the preliminary press area 22. The press ram 26 presses on a blank 28 of ceramic dental material which, in the state shown in FIG. 1, already extends partially into the press channels 18 and 20.

According to the invention, the material of the muffle 12 is composed of a relatively hard and heat-resistant plaster mix 30. The shape of the hollow cavities 14 and 16 is maintained even under the pressure of the force applied by the press ram 26, with the result that the dental restoration parts can be produced with the desired precision.

It will be appreciated that the embedding compound 30 is produced in any desired and suitable manner. It is particularly expedient for the hollow cavities 14 and 16 to be arranged relatively centrally in the embedding compound, so that good lateral support is ensured via the surrounding embedding compound 30.

According to the invention, provision is made for the hollow cavities 14 and 16 to be filled using a comparatively high pressing force, and thus a correspondingly high speed of penetration. The control according to the invention ensures, however, that good-quality dental restorations can be created.

It is also particularly expedient that, with a short dwell time of the hot dental material in the muffle, the inclination to reactions between the dental material and the embedding compound is low.

It will also be seen from FIG. 1 that the dental material 28 undergoes deformation as it enters the press channels 18 and 22. Typically, as can be seen at 34, a convex leading edge of the dental material 28 develops, because of the friction between the wall of the press channel 18 and the dental material.

Figure 2:
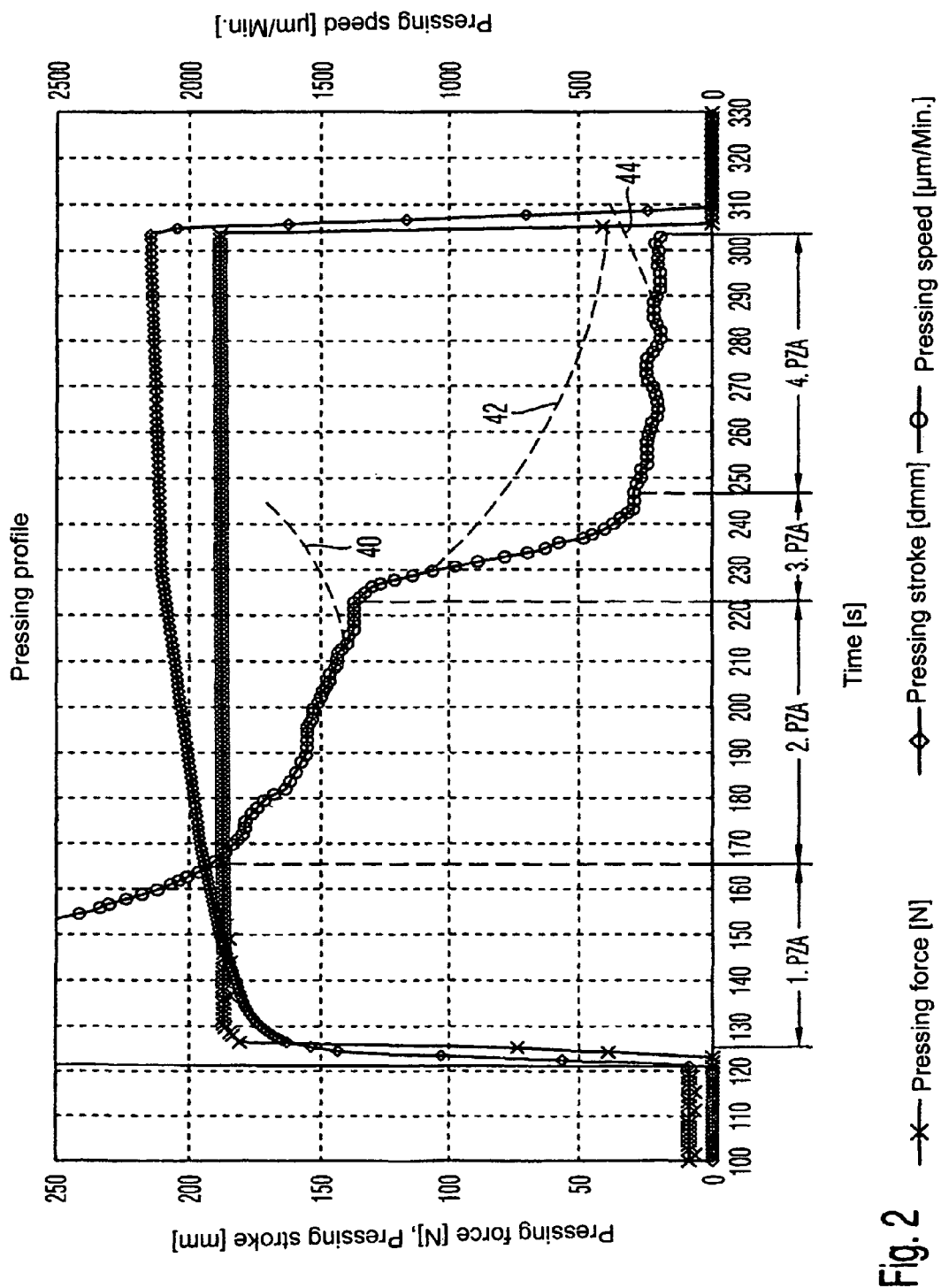
FIG. 2 shows a view of a profile according to the invention of the speed of penetration, plotted over time.

FIG. 2 shows how the speed of penetration, the pressing force and the position of the press ram develop during a pressing cycle. As can be seen, the press ram is activated at the time t=120 seconds. The pressing force increases to the nominal value of 200 N by approximately the time t=130 seconds.

During this time, the press ram pushes the blank 28 downward through the preliminary press area 20, the speed of penetration being extremely high, since there is practically no resistance. This is made clear in FIG. 2 from the fact that the curve of the speed of penetration is above 3000 mm/minute, namely at the maximum value of the spindle drive of the press ram.

The blank has reached the entry to the press channels 18 by about t=125 seconds. From this point in time onward, there is a considerably slower shifting of the position of the press ram, as is evident from the curve showing the press stroke.

The press channels 18 and 20 are filled, and, because of the press force remaining constant at 200 N, this is associated with a significant drop in the speed of penetration or speed of pressing.

At about t=165 seconds, the decrease in the speed of penetration or speed of pressing decreases much less markedly. The first pressing time phase is concluded at this point, and the leading edge of the dental material has passed completely through the press channels 18 and 20. The dental material now moves into the hollow cavities 14 and 16, where there is practically no increase or only a minimal increase in the frictional forces of the wall. This is reflected by the fact that the speed of penetration from t=160 seconds to approximately t=210 seconds drops only from 1900 mm/minute to 1400 mm/minute.

At the time t=210 seconds, the hollow cavities 14 and 16 are almost completely filled. Accordingly, the speed of penetration decreases quite rapidly again, so that the second pressing time phase to 210 seconds is followed by a third pressing time phase to t=245 seconds, in which the speed of penetration drops to approximately 300 mm/minute, always provided the pressing force remains constant.

At this point in time, air bubbles and the like are also largely forced out of dental material, and further solidification and sintering of the of the particulate and ceramic dental material takes place over a predetermined time period which, in the example illustrated, runs from t=245 seconds to t=305 seconds as the fourth pressing time phase, or so-called repressing time.

At this point, the press ram has reached its lowermost position, approximately at 215 mm. The pressing force and the pressing cycle are abruptly switched off and the ram is raised, so that the phase of cooling of the dental restoration in the muffle can begin.

According to the invention, an error signal is output in the event of a fundamental deviation of the speed of penetration or speed of pressing from the profile shown here.

For this purpose, the speed of penetration is preferably measured over fairly short time intervals, but averaged over a time period of 7 seconds for example, which, however, can also be chosen to be shorter or longer than this.

When the muffle already bursts toward the end of the second pressing time phase, there is an increase in the speed of penetration, for example from t=220 seconds, as shown by the curve 40. The forward movement of the press ram is in this case immediately suppressed, so that the muffle parts are not pressed away to the sides and do not damage the furnace or at least the thermocouple.

If the deviation from the intended pressing speed takes place only in the third pressing time phase, for example according to the curve 42, it can still be assumed that the cavities 14 and 16 are completely filled. In this case, the dental restoration is in principle usable, and in cases where there are a large number of hollow cavities, corresponding to simultaneously produced dental restoration parts, it is also possible that just some of the restorations can be used.

As can be seen from FIG. 2, the curve of the error-based speed of penetration 42 can extend substantially horizontally at first. Such a curve profile is possible if, for example, a void is enclosed within the embedding compound and the corresponding hollow cavity is then likewise filled into the hollow cavities 14 and 16. This profile of the speed of penetration is much less dangerous in terms of furnace damage than is the profile of the curve 40, since the muffle itself is initially intact on its outside and to this extent is not completely burst. It will be appreciated, however, that this bursting may take place at a later time.

If the speed of penetration follows the curve 44 according to FIG. 2, this typically indicates that at least almost all the dental restorations in the hollow cavities 14 and 16, and if appropriate in the further hollow cavities, are usable. They have then practically gone through the entire repressing time, and the final strength corresponds substantially to the desired final strength. However, in this case too, care should be taken to ensure that the system is switched off at the latest by the time t=305 seconds, which in turn avoids inadvertent damage to the press furnace.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A method for controlling a furnace for deforming a deformable dental material in a mold wherein the dental material is initially introduced into a preliminary press cavity in the mold, the press cavity being connected to a mold cavity, and monitoring movement parameters of the ram used to press the dental material from the press cavity into the mold cavity, the method comprising:

providing a control unit in which a standard parameter of speed of penetration of the press ram and/or injection force of the press ram is stored;

applying a force to the press ram to deform the dental material by pressing it through the preliminary press cavity and then into the mold cavity under an influence of heat;

measuring a time and/or the force with which the press ram covers a defined path as the force is applied to the press ram to determine either the speed of penetration of the press ram and/or a decrease in the injection force of the press ram, the measuring being done either continuously or recurrently at regular time intervals;

using the control unit to compare the speed of penetration and/or injection force with the stored standard press ram speed of penetration parameter and/or the injection force parameter, which comparing is done either continuously or recurrently at regular time intervals;

outputting a discontinuation signal via which the movement of the press ram is interrupted in the event that the speed of penetration of the press ram and/or the injection force of the press ram deviates from the stored standard parameter due to a burst in the mold; and determining whether the dental material is usable as a dental restoration part based upon the time at which the mold burst, if a discontinuation signal is output.

2. The method as claimed in 1, wherein the press ram is acted upon with a predetermined constant force, and the movement of the press ram is monitored starting from a start signal of a pressing cycle.

3. The method as claimed in 1, wherein the speed of penetration of the press ram is substantially constant near 0 (zero) toward the end of a repressing time, and, if the speed of penetration deviates from constancy, that is to say upon renewed increase of the speed of penetration, the discontinuation signal is output.

4. A furnace assembly for deforming a deformable dental material; the furnace assembly comprising:
- a mold provided with a preliminary press cavity which initially receives the deformable dental material, a mold cavity, and press channels extending between the preliminary press cavity and the mold cavity;
- a heater;
- a movable press ram to act on the dental material initially placed in the preliminary press cavity;
- a press drive configured to act on the press ram to deform the material by pressing it into the mold cavity under an influence of heat;
- a control unit that detects and stores either speed of penetration of the press ram or injection force of the press ram and, compares either continuously or recurrently at regular time intervals, movement parameters of the press ram during the pressing step with established press ram movement parameters;
- wherein when either an increase in the speed of the press ram or a decrease in the injection force of the press ram is detected due to a burst in the mold, outputs a signal which indicates an error and causes the press drive to be immediately stopped;
- wherein the control unit is configured to determine whether the dental material is usable as a dental restoration part based upon a time at which the mold burst, if a discontinuation signal is output.

5. The press furnace as claimed in claim 4 wherein the speed of penetration of the press ram and/or the injection force is detected via the force generating device.

* * * * *

UNITED STATES PATENT AND TRADEMARK OFFICE
CERTIFICATE OF CORRECTION

PATENT NO. : 8,465,681 B2  
APPLICATION NO. : 11/975480  
DATED : June 18, 2013  
INVENTOR(S) : Jussel et al.

Page 1 of 1

It is certified that error appears in the above-identified patent and that said Letters Patent is hereby corrected as shown below:

In the claims:

Column 6, line 64, in claim 1, "interrupted in the" should read:

--interrupted in an--.

Signed and Sealed this  
Seventeenth Day of September, 2013

Teresa Stanek Rea  
*Deputy Director of the United States Patent and Trademark Office*